United States Patent [19]

Tomotake et al.

[11] Patent Number: 5,399,474
[45] Date of Patent: Mar. 21, 1995

[54] LIGHT-SENSITIVE SILVER HALIDE COLOR PHOTOGRAPHIC MATERIAL

[75] Inventors: Atsushi Tomotake; Yutaka Kaneko, both of Hino, Japan

[73] Assignee: Konica Corporation, Tokyo, Japan

[21] Appl. No.: 273,973

[22] Filed: Jul. 11, 1994

Related U.S. Application Data

[63] Continuation of Ser. No. 37,084, Mar. 25, 1993, abandoned.

[30] Foreign Application Priority Data

Mar. 31, 1992 [JP] Japan .................. 4-077214

[51] Int. Cl.6 ................................. G03C 7/36
[52] U.S. Cl. ...................... 430/557; 430/389
[58] Field of Search .................. 430/557, 389

[56] References Cited

U.S. PATENT DOCUMENTS

| | | | |
|---|---|---|---|
| 4,314,023 | 2/1982 | Kojima et al. | 430/557 |
| 5,070,003 | 12/1991 | Naruso et al. | 430/557 |
| 5,215,877 | 6/1993 | Tomotake et al. | 430/557 |

FOREIGN PATENT DOCUMENTS

| | | | |
|---|---|---|---|
| 0475615 | 3/1992 | European Pat. Off. | |
| 2213461 | 11/1972 | Germany | 430/557 |
| 2429637 | 1/1975 | Germany | |
| 2600166 | 7/1976 | Germany | 430/557 |
| 50-6341 | 1/1975 | Japan | |
| 50-132926 | 10/1975 | Japan | |
| 52-115219 | 9/1977 | Japan | |
| 63-123047 | 5/1988 | Japan | |
| 3-125140 | 5/1991 | Japan | |
| 3-125141 | 5/1991 | Japan | |
| 3-209241 | 9/1991 | Japan | |
| 3-209242 | 9/1991 | Japan | |
| 3-209243 | 9/1991 | Japan | |
| 3-209244 | 9/1991 | Japan | |
| 3-209460 | 9/1991 | Japan | |
| 3-209461 | 9/1991 | Japan | |
| 3-209462 | 9/1991 | Japan | |
| 3-209463 | 9/1991 | Japan | |
| 3-209464 | 9/1991 | Japan | |
| 3-209465 | 9/1991 | Japan | |
| 3-209466 | 9/1991 | Japan | |
| 3-209467 | 9/1991 | Japan | |
| 3-209470 | 9/1991 | Japan | |
| 3-211548 | 9/1991 | Japan | |
| 3-211549 | 9/1991 | Japan | |
| 3-229248 | 10/1991 | Japan | |
| 4-124661 | 4/1992 | Japan | |
| 2078988 | 1/1982 | United Kingdom | |

Primary Examiner—Lee C. Wright
Attorney, Agent, or Firm—Frishauf, Holtz, Goodman & Woodward

[57] ABSTRACT

Disclosed is a light-sensitive silver halide color photographic material having at least one silver halide emulsion layer on a support, which comprises a two-equivalent yellow coupler represented by the following formula:

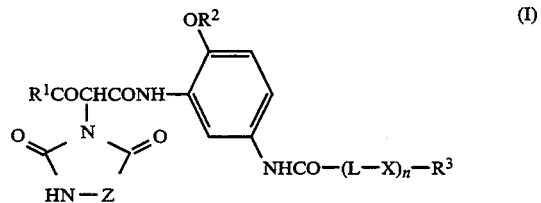

wherein $R^1$ and $R^2$ each represent an alkyl group or a cycloalkyl group; L represents an alkylene group; X represents a divalent linking group; $R^3$ represents an unsubstituted alkyl group or cycloalkyl group; n represents 0 or 1; and Z represents $>C(R^4)R^5$ or $>NR^4$ where $R^4$ and $R^5$ each represent a hydrogen atom or a substituent, being contained in at least one of the above silver halide emulsion layers.

16 Claims, No Drawings

LIGHT-SENSITIVE SILVER HALIDE COLOR PHOTOGRAPHIC MATERIAL

This application is a continuation of application Ser. No. 08/037,084, filed Mar. 25, 1993 (abandoned).

BACKGROUND OF THE INVENTION

This invention relates to a light-sensitive silver halide color photographic material, more specifically to a light-sensitive silver halide color photographic material using a novel two-equivalent yellow coupler which can be produced inexpensively and has excellent activity and also excellent image storability in a silver halide emulsion layer.

In recent years, in a light-sensitive silver halide color photographic material (hereinafter sometimes simply referred to as "a light-sensitive color material"), a two-equivalent coupler in which only two atoms of silver for forming one molecule of a dye are required by introducing a suitable substituent to coupling positions (active points) of a coupler which reacts with an oxidized product of a developing agent has been employed frequently in place of a conventional four-equivalent coupler which requires four atoms of silver for forming one molecule of a dye.

However, requirements of a coupler have become more strict with the progress of a light-sensitive color material. Not only improvement of activity but also further improvements of color reproducibility, image storability, solubility in low-boiling point and high-boiling point solvents and dispersion stability have been demanded.

As techniques for improving color reproducibility and activity, there has been known a yellow coupler having a heterocyclic compound with a cyclic imide structure as an eliminatable group and having an alkoxy group introduced to 2-position of an anilide portion. For example, in Japanese Provisional Patent Publication No. 115219/1977, there is described a yellow coupler having an alkoxy group at 2-position of an anilide portion and having a hydantoin group or an urazol group as an eliminatable group. However, this coupler involves a drawback that light resistance is extremely poor due to a sulfamoyl group existing as a ballast group.

As techniques for improving light resistance while maintaining good color reproducibility, there have been known, for example, yellow couplers having an alkoxy group at 2-position and an acylamino group at 5-position of an anilide portion and having a hydantoin group or an urazol group as an eliminatable group as described in Japanese Provisional Patent Publications No. 6341/1975, No. 123047/1988, No. 125140/1991, No. 125141/1991 and No. 124661/1992. However, in these couplers, activity is slightly poor, so that they cannot satisfy the recent demand for heightening activity sufficiently.

As one means for further improving activity, there has been known a technique of increasing hydrophilicity of an eliminatable group. For example, in Japanese Provisional Patent Publication No. 132926/1975, there is described a yellow coupler in which 2-position and 5-position of an anilide portion are substituted by an alkoxy group and an aryloxy group-substituted alkylacylamino group, respectively, and an unsubstituted urazol group is present at a nitrogen atom as an eliminatable group. Also, in Japanese Provisional Patent Publications No. 209241/1991, No. 209242/1991, No. 209243/1991, No. 209244/1991, No. 209460/1991, No. 209461/1991, No. 209462/1991, No. 209463/1991, No. 209464/1991, No. 209265/1991, No. 209466/1991, No. 209467/1991, No. 209470/1991, No. 211548/1991, No. 211549/1991 and No. 229248/1991, there are described yellow couplers in which 2-position and 5-position of an anilide portion are substituted by an aryloxy group and an unsubstituted alkylacylamino group, respectively, and an unsubstituted hydantoin group is present at a nitrogen atom as an eliminatable group. However, in these couplers, hydrophilicity of the eliminatable group is offset by the aryloxy group existing as a substituent so that activity has not yet reached a sufficiently satisfactory level.

SUMMARY OF THE INVENTION

The present invention has been made in consideration of the above problems. A first object of the present invention is to provide a light-sensitive silver halide color photographic material containing a novel two-equivalent coupler which can be produced inexpensively and having excellent activity.

A second object of the present invention is to provide a light-sensitive silver halide color photographic material containing a novel two-equivalent yellow coupler giving a sharp visible absorption spectrum necessary for excellent image storability (particularly excellent light resistance) and also faithful color reproducibility by reacting with an oxidized product of a developing agent at the time of color development, and forming a dye giving a sharp color image.

The above objects of the present invention can be accomplished by a light-sensitive silver halide color photographic material having at least one silver halide emulsion layer on a support, which comprises a two-equivalent yellow coupler represented by the following formula (I):

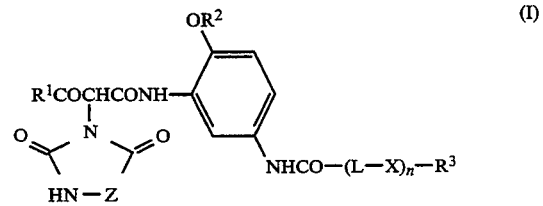

wherein $R^1$ and $R^2$ each represent an alkyl group or a cycloalkyl group; L represents an alkylene group; X represents a divalent linking group; $R^3$ represents an unsubstituted alkyl group or cycloalkyl group; n represents 0 or 1; and Z represents $>C(R^4)R^5$ or $>NR^4$ where $R^4$ and $R^5$ each represent a hydrogen atom or a substituent, being contained in at least one of the above silver halide emulsion layers.

DESCRIPTION OF THE PREFERRED EMBODIMENTS

In the following, the present invention is explained in detail.

In the above formula (I), the alkyl group represented by $R^1$ or $R^2$ may include a straight or branched alkyl group preferably having 1 to 15 carbon atoms, more preferably 1 to 6 carbon atoms, for example, a methyl group, an ethyl group, an i-propyl group, a t-butyl group, an n-dodecyl group and a 1-hexylnonyl group. The cycloalkyl group represented by $R^1$ or $R^2$ preferably has 3 to 10 carbon atoms, more preferably 3 to 6 carbon atoms, and may include a cyclopropyl group, a cyclohexyl group and an adamantyl group. These alkyl and cycloalkyl groups represented by $R^1$ or $R^2$ may further have a substituent(s). As the substituent, there may be mentioned, for example, a halogen atom (e.g. a chlorine atom and a bromine atom), a cyano group, a nitro group, an aryl group (e.g. a phenyl group, a p-t-octylphenyl group and a 2,4-di-t-amylphenyl group), a hydroxy group, an alkoxy group (e.g. a methoxy group and a 2-ethoxyethoxy group), an aryloxy group (e.g. a phenoxy group, a 2,4-di-t-amylphenoxy group and a 4'-(4'-hydroxyphenylsulfonyl)phenoxy group), a heterocyclic oxy group (e.g. a 4-pyridyloxy group and a 2-hexahydropyranyloxy group), a carbonyloxy group (e.g. an alkylcarbonyloxy group such as an acetyloxy group and a pivaloyloxy group, and an aryloxy group such as a benzoyloxy group), a sulfonyloxy group (e.g. an alkylsulfonyloxy group such as a methanesulfonyloxy group, a trifluoromethanesulfonyloxy group and an n-dodecanesulfonyloxy group, and an arylsulfonyloxy group such as a benzenesulfonyloxy group and a p-toluenesulfonyloxy group), a carbonyl group (e.g. an alkylcarbonyl group such as an acetyl group and a pivaloyl group, and an arylcarbonyl group such as a benzoyl group and a 3,5-di-t-butyl-4-hydroxybenzoyl group), an oxycarbonyl group (e.g. an alkoxycarbonyl group such as a methoxycarbonyl group, a cyclohexyloxycarbonyl group and an n-dodecyloxycarbonyl group, an aryloxycarbonyl group such as a phenoxycarbonyl group, a 2,4-di-t-amylphenoxycarbonyl group and a 1-naphthyloxycarbonyl group, and a heterocyclic oxycarbonyl group such as a 2-pyridyloxycarbonyl group and a 1-phenyl-pyrazolyl-5-oxycarbonyl group), a carbamoyl group (e.g. an alkylcarbamoyl group such as a dimethylcarbamoyl group and a 4-(2,4-di-t-amylphenoxy)butylaminocarbonyl group, and an arylcarbamoyl group such as a phenylcarbamoyl group and a 1-naphthylcarbamoyl group), a sulfonyl group (e.g. an alkylsulfonyl group such as a methanesulfonyl group and a trifluoromethanesulfonyl group, and an arylsulfonyl group such as a p-toluenesulfonyl group), a sulfamoyl group (e.g. an alkylsulfamoyl group such as a dimethylsulfamoyl group and a 4-(2,4-di-t-amylphenoxy)butylaminosulfonyl group, and an arylsulfamoyl group such as a phenylsulfamoyl group), an amino group (e.g. an alkylamino group such as a dimethylamino group, a cyclohexylamino group and an n-dodecylamino group, and an arylamino group such as an anilino group and a p-t-octylanilino group), a sulfonylamino group (e.g. an alkylsulfonylamino group such as a methanesulfonylamino group, a heptafluoropropanesulfonylamino group and an n-hexadecylsulfonylamino group, and an arylsulfonylamino group such as a p-toluenesulfonylamino group and a pentafluorobenzenesulfonylamino group), an acylamino group (e.g. an alkylcarbonylamino group such as an acetylamino group and a myristoylamino group, and an arylcarbonylamino group such as a benzoylamino group), an alkylthio group (e.g. a methylthio group and a t-octylthio group), an arylthio group (e.g. a phenylthio group) and a heterocyclic thio group (e.g. a 1-phenyltetrazole-5-thio group and a 5-methyl-1,3,4-oxadiazole-2-thio group).

$R^1$ is preferably an alkyl group, more preferably a branched alkyl group, particularly preferably a t-butyl group.

$R^2$ is preferably an alkyl group, more preferably an unsubstituted alkyl group, particularly preferably a methyl group.

In the above formula (I), the alkylene group represented by L may include a straight or branched alkylene group preferably having 1 to 10 carbon atoms, particularly preferably 1 to 4 carbon atoms, for example, a methylene group, an ethylene group, a 2,3-propylene group and a 1,2-cyclohexylene group.

In the above formula (I), the divalent linking group represented by X may include, for example, a sulfinyl group, a sulfenyl group, a sulfonyl group, a sulfamoyl group, a carbonyl group, a carbonyloxy group, a carbamoyl group, an oxy group, an oxycarbonyl group, an amino group, an acylamino group and a sulfonylamino group. Among these linking groups, preferred are a sulfonyl group, a sulfamoyl group, a carbonyloxy group, a carbamoyl group, an oxy group, an oxycarbonyl group and an acylamino group, and particularly preferred are a sulfonyl group, a carbonyloxy group and a carbamoyl group.

In the above formula (I), n represents 0 or 1, preferably 0.

In the above formula (I), $R^3$ is an unsubstituted alkyl group or cycloalkyl group, and may include, for example, the same groups mentioned as the alkyl group and cycloalkyl group represented by $R^1$ or $R^2$ in the above formula (I). Among them, $R^3$ is preferably an alkyl group, more preferably a straight alkyl group, particularly preferably a straight alkyl group having 15 to 21 carbon atoms.

In the above formula (I), Z represents $>C(R^4)R^5$ or $>NR^4$. Here, the substituent represented by $R^4$ or $R^5$ may include, for example, the same groups mentioned as the substituent represented by $R^3$ in the above formula (I). These substituents may further have a substituent(s). As the substituent, there may be mentioned, for example, the same groups mentioned as the substituent represented by $R^3$ in the above formula (I). These substituents represented by $R^4$ or $R^5$ may be the same or different, and may be bonded to each other to form a cyclic structure.

In the above formula (I), when Z is $>C(R^4)R^5$, the substituent represented by $R^4$ or $R^5$ is preferably an alkyl group, an alkoxy group, an amino group and a sulfonyl group, more preferably an alkyl group, particularly preferably a methyl group.

The two-equivalent yellow coupler represented by the above formula (I) may be bonded to either one of the substituents to form a bis product, a tris product, a tetrakis product or a polymer product.

In the following, representative examples of the two-equivalent yellow coupler represented by the formula (I) to be used in the present invention are shown, but the present invention is not limited thereto.

TABLE 1
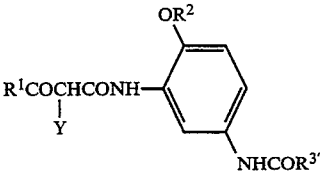

TABLE 1-continued $$\text{R}^1\text{COCHCONH}\underset{Y}{|}\text{—}\underset{\underset{\text{NHCOR}^{3'}}{|}}{\overset{\overset{\text{OR}^2}{|}}{\bigcirc}}$$

| No. | R$^1$ | R$^2$ | R$^{3'}$ | Y |
|---|---|---|---|---|
| (9) | t-C$_4$H$_9$ | CH$_3$ | —CH$_2$CH$_2$CONHC$_{14}$H$_{29}$ | 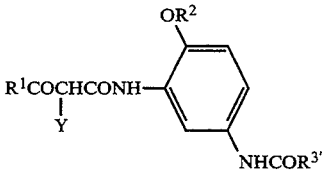 |
| (10) | t-C$_4$H$_9$ | CH$_3$ | —CH$_2$CH$_2$NHCOC$_{13}$H$_{27}$ | 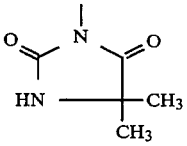 |
| (11) | t-C$_4$H$_9$ | CH$_2$COOC$_{12}$H$_{25}$ | —CH$_3$ | 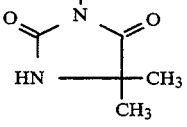 |
| (12) | t-C$_4$H$_9$ | CH$_3$ | —C$_{17}$H$_{35}$ | 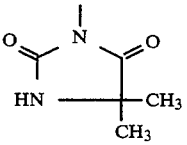 |
| (13) | t-C$_4$H$_9$ | CH$_3$ | —C$_{15}$H$_{31}$ | 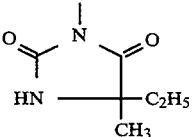 |
| (14) | t-C$_4$H$_9$ | CH$_3$ | —CHCH$_2$SO$_2$C$_{12}$H$_{25}$<br>   \|<br>   CH$_3$ | 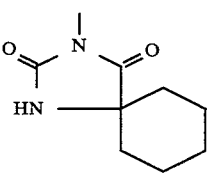 |
| (15) | t-C$_4$H$_9$ | CH$_3$ | —C$_{13}$H$_{27}$ | 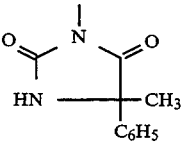 |
| (16) | t-C$_4$H$_9$ | CH$_3$ | —C$_{17}$H$_{35}$ | 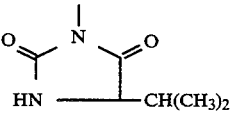 |
| (17) | t-C$_4$H$_9$ | CH$_3$ | —C$_{15}$H$_{31}$ | 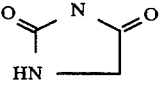 |

TABLE 1-continued $$R^1COCHCONH-\underset{Y}{}\text{[benzene ring with }OR^2\text{ ortho and }NHCOR^{3'}\text{ para]}$$

| No. | R¹ | R² | R³′ | Y |
|---|---|---|---|---|
| (18) | t-C₄H₉ | C₂H₅ | —C₁₅H₃₁ | 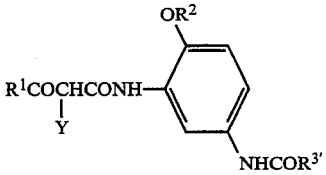 |
| (19) | t-C₄H₉ | cyclopropyl | —C₁₇H₃₅ | 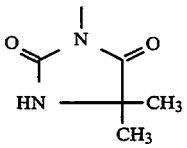 |
| (20) | t-C₄H₉ | CH₂CH₂OH | —C₁₇H₃₅ |  |
| (21) | 1-methylcyclopropyl | CH₃ | —C₁₃H₂₇ | 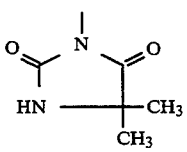 |
| (22) | adamantyl | CH₃ | —C₁₅H₃₁ | 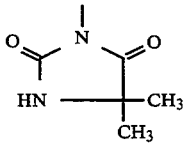 |
| (23) | t-C₄H₉ | CH₃ | —C₁₇H₃₅ |  |
| (24) | t-C₄H₉ | CH₃ | —CHCH₂SO₂C₁₂H₂₅<br>    \|<br>    CH₃ | 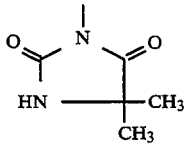 |
| (25) | t-C₄H₉ | CH₃ | $\begin{array}{l}\phantom{-}CH_3\\-CHCHCH_2C(CH_3)_3\\\phantom{-CH}|\\\phantom{-}CH_2CH_2CHCH_2C(CH_3)_3\\\phantom{-CH_2CH_2CH}|\\\phantom{-CH_2CH_2CH}CH_3\end{array}$ | 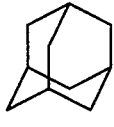 |

TABLE 1-continued

R¹COCHCONH— [benzene with OR² and NHCOR³']
|
Y

| No. | R¹ | R² | R³' | Y |
|-----|------|-----|---------|---|
| (26) | t-C₄H₉ | CH₃ | —C₁₇H₃₅ | hydantoinyl-N-(4-methoxyphenyl) |
| (27) | t-C₄H₉ | CH₃ | —C₁₇H₃₅ | hydantoinyl-N-(4-cyanophenyl) |
| (28) | (polymer structure with t-C₄H₉COCHCONH—, OCH₂COOCH₂CH₂CH₂—, NHCOC₁₃H₂₇, 5,5-dimethylhydantoinyl, subscript 2) | | | |

The yellow coupler represented by the formula (I) of the present invention can be synthesized easily according to a conventionally known method by using an easily and commercially available compound as a starting material. In the following, a representative specific synthesis example of of the present invention is shown.

Synthesis Example: Synthesis of Exemplary Coupler (1)

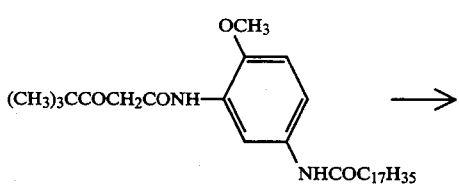

Four-equivalent coupler (A)

→

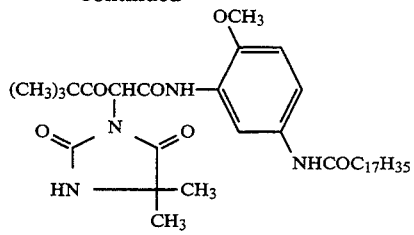

Exemplary coupler (1)

In 50 ml of chloroform was dissolved 5.3 g of the four-equivalent coupler (A), and 2.0 g of sulfuryl chloride was added dropwise thereto at room temperature. After the dropwise addition, the mixture was stirred for 1 hour under the same conditions, and the reaction mixture was washed with water. The washed organic layer was dried over anhydrous magnesium sulfate, and the solvent was removed under reduced pressure.

The resulting residue was dissolved in 50 ml of acetone, and 2.5 g of 5,5-dimethylhydantoin and 2.7 g of potassium carbonate were added thereto. The mixture was refluxed by heating for 2 hours. After the insolubles were removed by filtration, the solvent was removed under reduced pressure. The residue was dissolved in 100 ml of ethyl acetate, and the mixture was washed with a 5% potassium carbonate aqueous solution and with diluted hydrochloric acid. After the organic layer was dried over anhydrous magnesium sulfate, the solvent was removed under reduced pressure. The residue was dissolved in 30 ml of methanol and recrystallized to obtain the desired Exemplary coupler (1). Resulting amount: 6.3 g (yield: 61%).

The structure of Exemplary coupler (1) was confirmed by NMR, IR and mass spectra.

Exemplary couplers other than Exemplary coupler (1) were synthesized from the corresponding starting materials, respectively, according to the method as in the above synthesis example.

The yellow coupler of the present invention can be used singly or in combination of two or more of them. Further, all known pivaloyl acetanilide type or benzoyl acetanilide type yellow couplers can be used in combination.

The yellow coupler of the present invention may be incorporated into a silver halide photographic emulsion of a light-sensitive color photographic material by, for example, dissolving the yellow coupler in at least one high-boiling point organic solvent having a boiling point of 175° C. or higher such as tricresyl phosphate or dibutyl phthalate and/or at least one low-boiling point organic solvent such as ethyl acetate, methanol, acetone, chloroform, methyl chloride or butyl propionate used at the time of preparing a coupler dispersion in the prior art, mixing the resulting solution with a gelatin aqueous solution containing a surfactant, subsequently emulsifying and dispersing the mixture by using a high-speed rotary mixer or a colloid mill, and then adding the resulting emulsified dispersion directly to the silver halide photographic emulsion, or setting and then shredding the above emulsified dispersion, removing the low-boiling point organic solvent by using a means such as washing, and then adding the resulting product to the silver halide photographic emulsion.

The yellow coupler of the present invention is generally added preferably in an amount of about $1 \times 10^{-3}$ mole to about 1 mole per mole of silver halide, but the amount to be added may be changed to the amount exceeding the above range depending on the purpose of its application.

The light-sensitive silver halide color photographic material of the present invention may be any light-sensitive material used for any purpose, and as the silver halide, there may be used, for example, silver chloride, silver bromide, silver iodide, silver chlorobromide, silver iodobromide and silver chloroiodobromide.

In the light-sensitive silver halide color photographic material of the present invention, other color couplers for forming a multicolor image can be contained together with the yellow coupler according to the present invention.

In the light-sensitive silver halide color photographic material of the present invention, there can be used a color antifoggant, an image stabilizer, a hardener, a plasticizer, a polymer latex, a formalin scavenger, a mordant, a development accelerator, a development retardant, a fluorescent brightener, a matting agent, a solvent, an antistatic agent and a surfactant as desired.

By incorporating a UV absorber into the light-sensitive silver halide color photographic material containing the yellow coupler of the present invention, fade resistance of a yellow image formed on the light-sensitive material can be further improved.

EXAMPLES

The present invention is described in detail by referring to Examples, but the embodiment of the present invention is not limited to these Examples.

On a paper support having one surface of which polyethylene was laminated and the other surface of which polyethylene containing titanium oxide was laminated, the respective layers having the following constitutions were provided by coating at the side of the surface on which polyethylene containing titanium oxide was laminated to prepare a multi-layer light-sensitive silver halide color photographic material 101. Coating solutions were prepared as described below.

First Layer Coating Solution

To 60 ml of ethyl acetate were added 24.4 g of Yellow coupler (1), 7.26 g of a dye image stabilizer (ST-1), 7.26 g of a dye image stabilizer (ST-2), 0.67 g of an additive (HQ-1), 0.33 g of an antiirradiation dye (AI-3) and 6.05 g of a high boiling point solvent (DNP) and the mixture was dissolved. The solution was emulsified and dispersed in 220 ml of a 10% gelatin aqueous solution containing 7 ml of a 20% surfactant (SU-1) by using an ultrasonic homogenizer to prepare a yellow coupler dispersion. The dispersion was mixed with a blue-sensitive silver halide emulsion (containing 8.68 g of silver) prepared under the following conditions to prepare a first layer coating solution.

Second layer to seventh layer coating solutions were prepared in the same manner as the above first layer coating solution.

As a hardener, (H-1) was added to the second layer and fourth layer, and (H-2) was added to the seventh layer. As a coating aid, surfactants (SU-2) and (SU-3) were added in order to control surface tension. In the following Examples, amounts added to the light-sensitive silver halide photographic material are represented by gram per 1 $m^2$ unless otherwise indicated.

TABLE 2

| Layer | Constitution | Amount added (g/m$^2$) |
| --- | --- | --- |
| Seventh layer (Protective layer) | Gelatin | 1.00 |
| | DIDP | 0.005 |
| | Additive (HQ-2) | 0.002 |
| | Additive (HQ-4) | 0.004 |
| | Additive (HQ-5) | 0.02 |
| | Additive (HQ-6) | 0.002 |
| | Compound (F-1) | 0.002 |
| Sixth layer (UV absorbing layer) | Gelatin | 0.04 |
| | UV absorber (UV-1) | 0.10 |
| | UV absorber (UV-2) | 0.04 |
| | UV absorber (UV-3) | 0.16 |
| | Additive (HQ-5) | 0.04 |
| | DNP | 0.20 |
| | PVP | 0.03 |
| | Antiirradiation dye (AI-2) | 0.02 |
| | Antiirradiation dye (AI-4) | 0.01 |
| Fifth layer (Red-sensitive layer) | Gelatin | 1.30 |
| | Red-sensitive silver chlorobromide emulsion (Em-R) | 0.21 |
| | Cyan coupler (C-1) | 0.17 |
| | Cyan coupler (C-2) | 0.25 |
| | Dye image stabilizer (ST-1) | 0.20 |
| | Additive (HQ-1) | 0.01 |
| | HBS-1 | 0.20 |
| | DOP | 0.20 |
| Fourth layer (UV absorbing layer) | Gelatin | 0.94 |
| | UV absorber (UV-1) | 0.28 |
| | UV absorber (UV-2) | 0.09 |
| | UV absorber (UV-3) | 0.38 |
| | Additive (HQ-5) | 0.10 |

TABLE 2-continued

| Layer | Constitution | Amount added (g/m²) |
|---|---|---|
| | DNP | 0.40 |
| Third layer (Green-sensitive layer) | Gelatin | 1.40 |
| | Green-sensitive silver chlorobromide emulsion (Em-G) | 0.17 |
| | Magenta coupler (M-1) | 0.23 |
| | Dye image stabilizer (ST-3) | 0.20 |
| | Dye image stabilizer (ST-4) | 0.17 |
| | DIDP | 0.13 |
| | DBP | 0.13 |
| | Antiirradiation dye (AI-1) | 0.01 |
| Second layer (Intermediate layer) | Gelatin | 1.20 |
| | Additive (HQ-2) | 0.03 |
| | Additive (HQ-3) | 0.03 |
| | Additive (HQ-4) | 0.05 |
| | Additive (HQ-5) | 0.23 |
| | DIDP | 0.06 |
| | Compound (F-1) | 0.002 |
| First layer (Blue-sensitive layer) | Gelatin | 1.20 |
| | Blue-sensitive silver chlorobromide emulsion (Em-B) | 0.26 |
| | Yellow coupler (Compound (1) of the present invention) | 0.73 |
| | Dye image stabilizer (ST-1) | 0.22 |
| | Dye image stabilizer (ST-2) | 0.22 |
| | Additive (HQ-1) | 0.02 |
| | Antiirradiation dye (AI-3) | 0.01 |
| | DNP | 0.18 |
| Support | Polyethylene-laminated paper | |

The amounts of the silver halide emulsions added are represented by calculating them on silver.

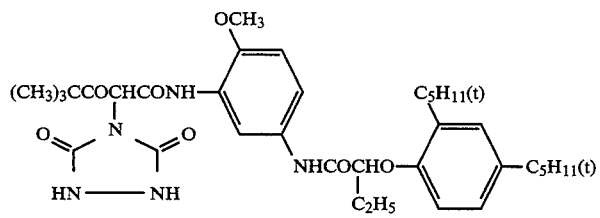

Comparative coupler Y-1

(Coupler described in Japanese Provisional Patent Publication No. 165145/1981)

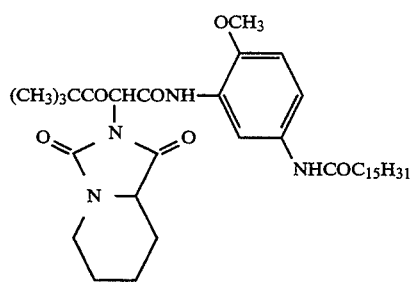

Comparative coupler Y-2

(Coupler described in Japanese Provisional Patent Publication No. 6341/1975)

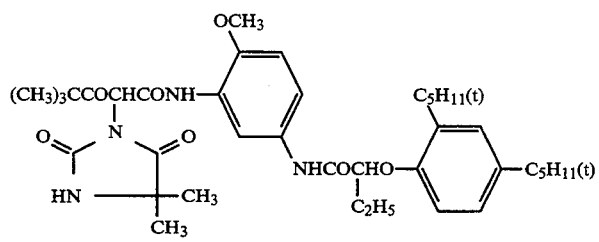

Comparative coupler Y-3

(Coupler described in Japanese Provisional Patent Publication No. 132926/1975)

-continued
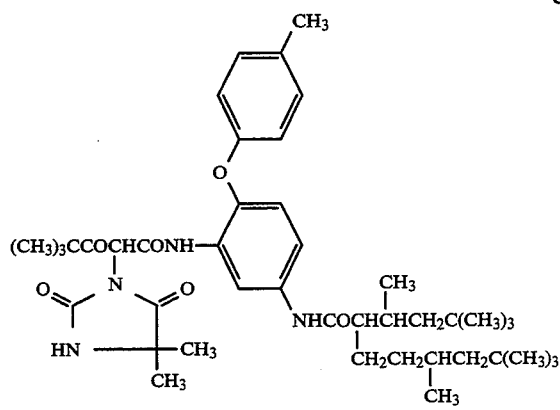
(Coupler described in Japanese Provisional Patent Publication No. 209241/1991)
Comparative coupler Y-4
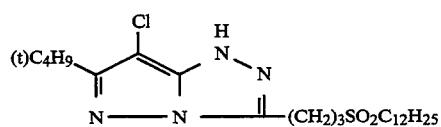
M-1
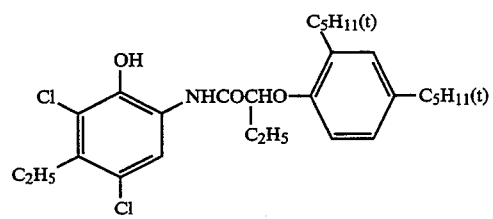
C-1
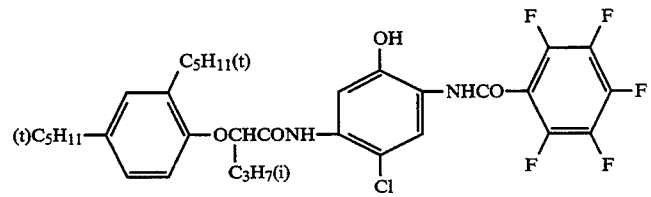
C-2
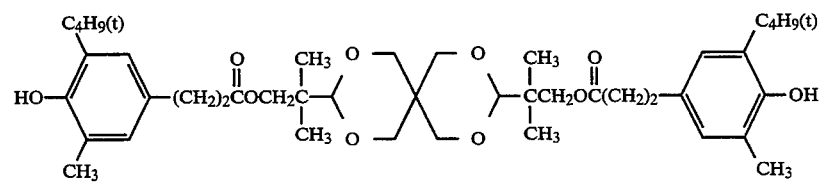
ST-1
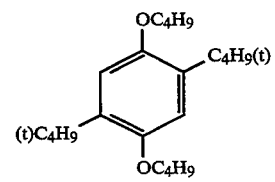
ST-2
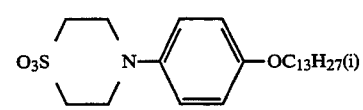
ST-3
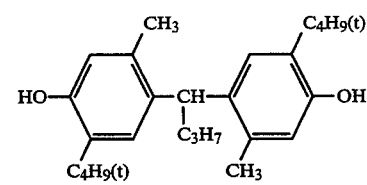
ST-4

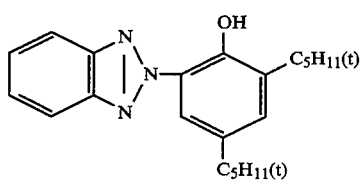 UV-1
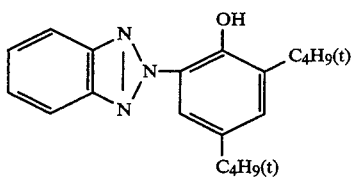 UV-2
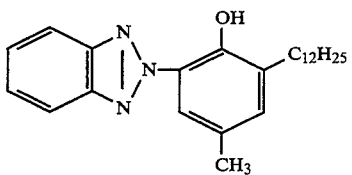 UV-3
DBP: Dibutyl phthalate
DOP: Dioctyl phthalate
DNP: Dinonyl phthalate
DIDP: Diisodecyl phthalate
PVP: Polyvinyl pyrrolidone
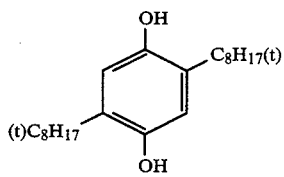 HQ-1
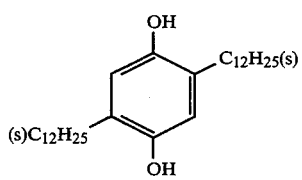 HQ-2
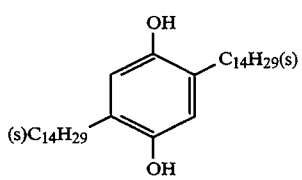 HQ-3
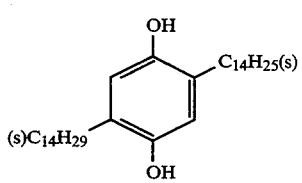 HQ-4
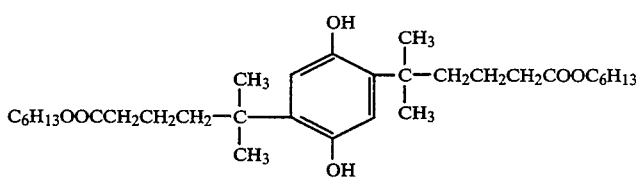 HQ-5
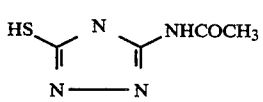 HQ-6

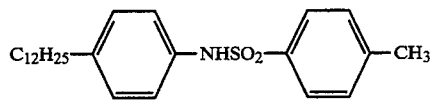
HBS-1
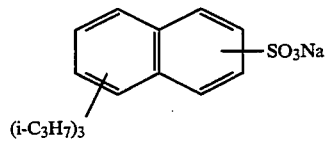
SU-1
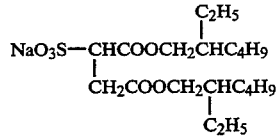
SU-2
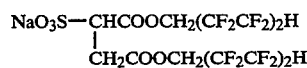
SU-3
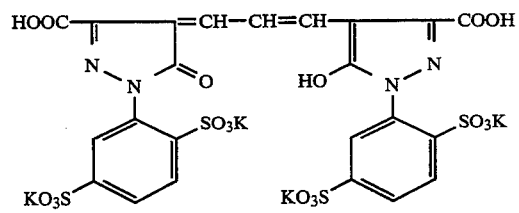
AI-1
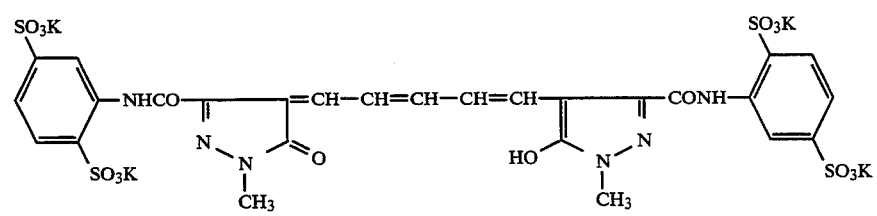
AI-2
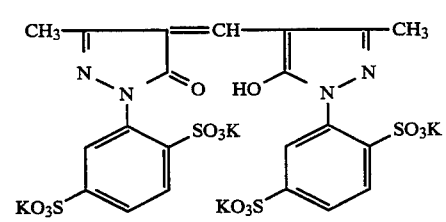
AI-3
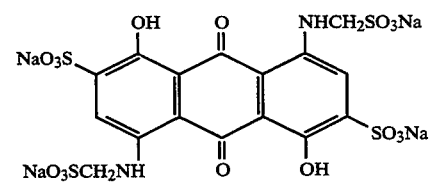
AI-4
H-1
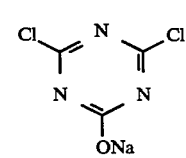
H-2

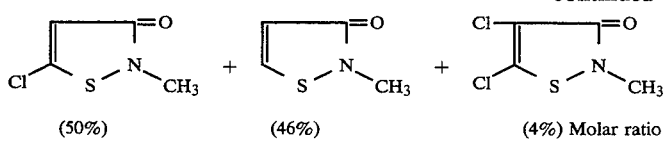

(50%)     (46%)     (4%) Molar ratio

F-1

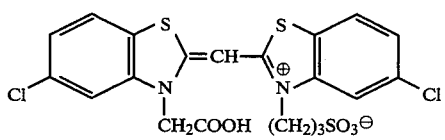

BS-1

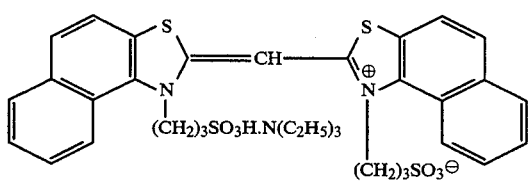

BS-2

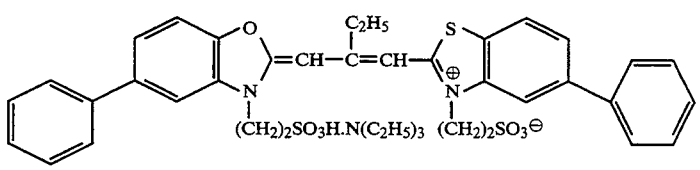

GS-1

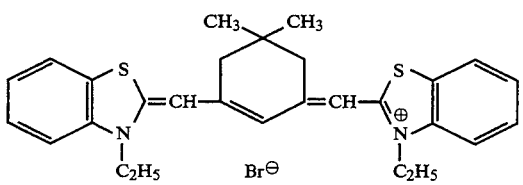

RS-1

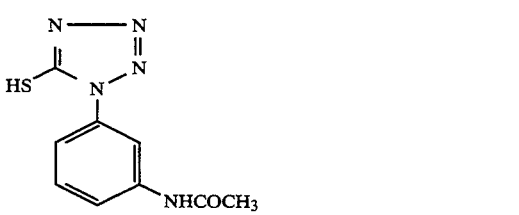

STAB-1

Preparation Method of Blue-Sensitive Silver Halide Emulsion

To 1,000 ml of a 2% gelatin aqueous solution maintained at 40° C. were added the following (Solution A) and (Solution B) simultaneously over 30 minutes while controlling pAg=6.5 and pH=3.0, and further added the following (Solution C) and (Solution D) simultaneously over 180 minutes while controlling pAg=7.3 and pH=5.5. The pH was controlled by using an aqueous solution of sulfuric acid or sodium hydroxide. The pAg was controlled by using a controlling solution having the following composition. The controlling solution is an aqueous solution of a halide mixture comprising sodium chloride and potassium bromide, and the ratio of a chloride ion to a bromide ion is 99.8:0.2. When Solution A and Solution B were added, the concentration of the controlling solution was 0.1 mole/liter, and when Solution C and Solution D were added, it was 1 mole/liter.

(Solution A)

| | |
|---|---|
| Sodium chloride | 3.42 g |
| Potassium bromide | 0.03 g |
| made up to 200 ml with addition of water. | |
| (Solution B) | |
| Silver nitrate | 10 g |
| made up to 200 ml with addition of water. | |
| (Solution C) | |
| Sodium chloride | 102.7 g |
| Potassium bromide | 1.0 g |
| made up to 600 ml with addition of water. | |
| (Solution D) | |
| Silver nitrate | 300 g |
| made up to 600 ml with addition of water. | |

After completion of the addition, desalting was carried out by using a 5% aqueous solution of Demol N (trade name) produced by Kao Atlas Co. and a 20% aqueous solution of magnesium sulfate, and then the mixture obtained was mixed with a gelatin aqueous solution to obtain a monodispersed cubic emulsion EMP-1 having an average grain size of 0.85 μm, a variation coefficient ($\sigma/r$) of 0.07 and a silver chloride content of 99.5 mole %.

The above emulsion EMP-1 was chemically ripened at 50° C. for 90 minutes by using the following compounds to obtain a blue-sensitive silver halide emulsion (Em-B).

| Sodium thiosulfate | 0.8 mg/mole of AgX |
|---|---|
| Chloroauric acid | 0.5 mg/mole of AgX |
| Stabilizer STAB-1 | $6 \times 10^{-4}$ mole/mole of AgX |
| Sensitizing dye BS-1 | $4 \times 10^{-4}$ mole/mole of AgX |
| Sensitizing dye BS-2 | $1 \times 10^{-4}$ mole/mole of AgX |

Preparation Method of Green-Sensitive Silver Halide Emulsion

In the same manner as EMP-1 except for changing addition time of (Solution A) and (Solution B) and addition time of (Solution C) and (Solution D), a monodispersed cubic emulsion EMP-2 having an average grain size of 0.43 μm, a variation coefficient ($\sigma/r$) of 0.08, and a silver chloride content of 99.5 mole % was prepared.

EMP-2 was chemically ripened at 55° C. for 120 minutes by using the following compounds to obtain a green-sensitive silver halide emulsion (Em-G)

| Sodium thiosulfate | 1.5 mg/mole of AgX |
|---|---|
| Chloroauric acid | 1.0 mg/mole of AgX |
| Stabilizer STAB-1 | $6 \times 10^{-4}$ mole/mole of AgX |
| Sensitizing dye GS-1 | $4 \times 10^{-4}$ mole/mole of AgX |

Preparation Method of Red-Sensitive Silver Halide Emulsion

In the same manner as EMP-1 except for changing addition time of (Solution A) and (Solution B) and addition time of (Solution C) and (Solution D), a monodispersed cubic emulsion EMP-3 having an average grain size of 0.50 μm, a variation coefficient ($\sigma/r$) of 0.08, and a silver chloride content of 99.5 mole % was prepared.

EMP-3 was chemically ripened at 60° C. for 90 minutes by using the following compounds to obtain a red-sensitive silver halide emulsion (Em-R)

| Sodium thiosulfate | 1.8 mg/mole of AgX |
|---|---|
| Chloroauric acid | 2.0 mg/mole of AgX |
| Stabilizer STAB-1 | $6 \times 10^{-4}$ mole/mole of AgX |
| Sensitizing dye RS-1 | $1 \times 10^{-4}$ mole/mole of AgX |

The variation coefficient is calculated from a standard deviation ($\sigma$) and an average grain size ($\bar{r}$) according to the following formula:

$$\sigma = \sqrt{\frac{\Sigma (\bar{r} - r_i)^2 n_i}{\Sigma n_i}}$$

wherein $r_i$ represents a grain size, $n_i$ represents a number of grains having a grain size of $r_i$ and $\bar{r}$ is an average grain size.

Processing conditions are shown below.

| Processing step | Temperature | Time |
|---|---|---|
| Color developing | 35.0 ± 0.3° C. | 45 sec |
| Bleach-fixing | 35.0 ± 0.5° C. | 45 sec |
| Stabilizing | 30 to 34° C. | 90 sec |
| Drying | 60 to 80° C. | 60 sec |

| -continued | |
|---|---|
| Color developing solution | |
| Pure water | 800 ml |
| Triethanolamine | 10 g |
| N,N-Diethylhydroxylamine | 5 g |
| Potassium bromide | 0.02 g |
| Potassium chloride | 2 g |
| Potassium sulfite | 0.3 g |
| 1-Hydroxyethylidene-1,1-diphosphonic acid | 1.0 g |
| Ethylenediaminetetraacetic acid | 1.0 g |
| Disodium catechol-3,5-disulfonate | 1.0 g |
| Diethylene glycol | 10 g |
| N-ethyl-N-β-methanesulfonamidoethyl-3-methyl-4-aminoaniline sulfate | 4.5 g |
| Fluorescent brightener (a 4,4'-diamino-stilbenesulfonic acid derivative) | 1.0 g |
| Potassium carbonate | 27 g |
| made up to 1 liter in total with addition of water, and adjusted to pH 10.10. | |
| Bleach-fixing solution | |
| Ferric ammonium ethylenediaminetetra-acetate dihydrate | 60 g |
| Ethylenediaminetetraacetic acid | 3 g |
| Ammonium thiosulfate (70% aqueous solution) | 100 ml |
| Ammonium sulfite (40% aqueous solution) | 27.5 ml |
| made up to 1 liter in total with addition of water, and adjusted to pH 5.7 with potassium carbonate or glacial acetic acid. | |
| Stabilizing solution | |
| 5-Chloro-2-methyl-4-isothiazolin-3-one | 0.2 g |
| 1,2-Benzisothiazolin-3-one | 0.3 g |
| Ethylene glycol | 1.0 g |
| 1-Hydroxyethylidene-1,1-diphosphonic acid | 2.0 g |
| o-Phenylphenol sodium | 1.0 g |
| Ethylenediaminetetraacetic acid | 1.0 g |
| Ammonium hydroxide (20% aqueous solution) | 3.0 g |
| Fluorescent brightener (a 4,4'-diamino-stilbenesulfonic acid derivative) | 1.5 g |
| made up to 1 liter in total with addition of water, and adjusted to PH 7.0 with sulfuric acid or potassium hydroxide. | |

Further, Samples 102 to 114 and Comparative samples 115 and were prepared in the same manner as Sample 101 except for changing the yellow coupler and the dye image stabilizer used in the first layer of Sample 101 as shown in Table 3. The amount of the yellow coupler to be added was controlled to the same molar amount as the amount of the yellow coupler added to Sample 101, and the amounts of the dye image stabilizers to be added were so controlled that the amount of a 1:1 mixture of ST-1 and ST-2 was 60% (molar ratio) of the amount of the yellow coupler added.

The samples thus prepared were subjected to wedge exposure with white light for 0.2 second and developed according to the processing steps described above. Thereafter, the maximum color density $D_{max}$ and the minimum color density $D_{min}$ were measured by using an optical densitometer Model PDA-65 (trade name, manufactured by Konica Corporation).

After the above samples were exposed with sunlight for 4 weeks, remaining density at the portion having an initial density of 1.0 was measured.

Also, the samples subjected to exposure and color development were allowed to stand at a dark place at the temperature of 85° C. and the humidity of 60% for two weeks, and then remaining density at the portion having an initial density of 1.0 was measured, respectively.

Further, after the color tone of the gray portion of the negative film obtained by photographing a color checker (produced by Macbeth Co.) by using Konica Color SDD100 (trade name, produced by Konica Corporation) and developing the film was modified, the film was printed on the samples prepared as described above. The samples were developed according to the processing steps described above, and color reproducibility of yellow was evaluated.

The results are shown in Table 3.

TABLE 3

| Sample | Coupler | $D_{max}$ | $D_{min}$ | Light resistance | Moist heat resistance | Color reproducibility* | Remarks |
|---|---|---|---|---|---|---|---|
| 101 | (1) | 2.44 | 0.14 | 0.91 | 0.97 | ○ | Present invention |
| 102 | (2) | 2.38 | 0.13 | 0.88 | 0.96 | ○ | Present invention |
| 103 | (4) | 2.33 | 0.16 | 0.84 | 0.94 | ○ | Present invention |
| 104 | (6) | 2.36 | 0.14 | 0.84 | 0.95 | ○ | Present invention |
| 105 | (7) | 2.35 | 0.15 | 0.87 | 0.92 | ○ | Present invention |
| 106 | (9) | 2.34 | 0.15 | 0.86 | 0.93 | ○ | Present invention |
| 107 | (10) | 2.31 | 0.17 | 0.86 | 0.93 | ○ | Present invention |
| 108 | (11) | 2.32 | 0.15 | 0.87 | 0.93 | ○ | Present invention |
| 109 | (12) | 2.42 | 0.14 | 0.91 | 0.98 | ○ | Present invention |
| 110 | (17) | 2.37 | 0.16 | 0.85 | 0.95 | ○ | Present invention |
| 111 | (20) | 2.30 | 0.20 | 0.81 | 0.96 | ○ | Present invention |
| 112 | (23) | 2.35 | 0.14 | 0.86 | 0.92 | ○ | Present invention |
| 113 | (24) | 2.33 | 0.16 | 0.83 | 0.92 | ○ | Present invention |
| 114 | (26) | 2.34 | 0.17 | 0.88 | 0.94 | ○ | Present invention |
| 115 | Y-1 | 2.25 | 0.22 | 0.82 | 0.62 | ○ | Comparative |
| 116 | Y-2 | 2.16 | 0.18 | 0.78 | 0.84 | ○ | Comparative |
| 117 | Y-3 | 2.23 | 0.18 | 0.81 | 0.64 | ○ | Comparative |
| 118 | Y-4 | 2.20 | 0.21 | 0.76 | 0.80 | Δ | Comparative |

○: Good color reproducibility (tone and chromaticness)
Δ: Insufficient color reproducibility (tone and chromaticness)

From the results shown in Table 3, it can be seen that in Comparative samples 115 and 117 using Comparative couplers Y-1 and Y-3 having an aryloxy substituent in a ballast group, activity is poor. Similarly, it can be seen that in Comparative sample 118 using Comparative coupler Y-4 having an aryloxy group on an anilide ring, activity and color reproducibility are also poor, and in Comparative sample 116 using Comparative coupler Y-2 having a substituent existing on a nitrogen atom of a hydantoin group which is an eliminatable group, activity is also poor. Further, it can be seen that all of these comparative samples have poor light resistance and markedly poor moist heat resistance.

To the contrary, it can be seen that in all of the present samples using the couplers of the present invention, the maximum color density is higher, an image dye less in fog can be formed, higher light resistance and higher moist heat resistance are exhibited and color reproducibility is more excellent as compared with the comparative samples.

The coupler of the present invention can be easily synthesized by using an easily and commercially available compound. Further, it has been clarified that by incorporating the coupler of the present invention into a light-sensitive color material, an image having high color density, less fog, good image storability and excellent color reproducibility can be obtained.

We claim:

1. A light-sensitive silver halide color photographic material comprising a support having thereon at least one silver halide emulsion layer containing a two-equivalent yellow coupler represented by the following formula:

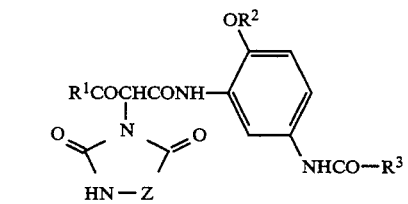

(I)

wherein $R^1$ and $R^2$ each represent an alkyl group or a cycloalkyl group; $R^3$ represents an unsubstituted alkyl group or cycloalkyl group; and Z represents $>C(R^4)R^5$ or $>NR^4$ where $R^4$ and $R^5$ each represent a hydrogen or a substituent.

2. The material of claim 1 wherein Z in the formula (I) is $>C(R^4)R^5$.

3. The material of claim 2 wherein $R^1$ is a t-butyl group; $R^2$, $R^4$ and $R^5$ are all methyl groups and $R^3$ is an alkyl group having 15 to 21 carbon atoms.

4. The material of claim 2 wherein $R^4$ is hydrogen.

5. The material of claim 2 wherein
$R^1$ is a t-butyl group;
$R^2$ is a methyl group;
$R^3$ is an alkyl group with 15 to 21 carbon atoms;
$R^4$ is hydrogen; and
$R^5$ is a methyl group or hydrogen.

6. The method of claim 5 wherein $R^5$ is hydrogen.

7. The method of claim 5 wherein $R^5$ is methyl.

8. The material of claim 1 wherein Z in the formula (I) is $>NR^4$.

9. The material of claim 8 wherein $R^1$ is a t-butyl group; $R^2$ and $R^4$ are both methyl groups and $R^3$ is an alkyl group having 15 to 21 carbon atoms.

10. The material of claim 8 wherein $R^4$ is hydrogen.

11. The method of claim 8 wherein
$R^1$ is a t-butyl group;
$R^2$ is a methyl group;
$R^3$ is an alkyl group with 15 to 21 carbon atoms; and
$R^4$ is hydrogen.

12. The material of claim 1 wherein the substituent $R^3$ in the formula (I) is a straight alkyl group.

13. The material of claim 12 wherein the substituent $R^3$ in the formula (I) is an alkyl group having 15 to 21 carbon atoms.

14. The material of claim 13 wherein the substituent $R^1$ in the formula (I) is a t-butyl group, and $R^2$, $R^4$ and $R^5$ are all methyl groups.

15. The material of claim 1 wherein $R^1$ is a t-butyl group, $R^2$ is a methyl group, $R^3$ is an alkyl group having 13, 15, 17 or 21 carbon atoms and Z is $>C(CH_3)_2$.

16. The material of claim 1 wherein $R^4$ is hydrogen.

* * * * *